United States Patent [19]
Fertig

[11] Patent Number: 4,866,681
[45] Date of Patent: Sep. 12, 1989

[54] PHOTO-ACOUSTIC DETECTOR

[75] Inventor: Glenn H. Fertig, Natrona Heights, Pa.

[73] Assignee: Mine Safety Appliances Company, Pittsburgh, Pa.

[21] Appl. No.: 165,750

[22] Filed: Mar. 9, 1988

[51] Int. Cl.⁴ .............................................. H04R 23/00
[52] U.S. Cl. .................................... 367/140; 250/345; 350/96.29; 356/432
[58] Field of Search ................ 367/140, 141; 250/345; 356/432, 437; 350/96.29; 73/643

[56] References Cited

U.S. PATENT DOCUMENTS

| | | | |
|---|---|---|---|
| 4,055,764 | 10/1977 | Dimeff | 250/343 |
| 4,193,695 | 3/1980 | Kojima et al. | 250/343 |
| 4,236,827 | 12/1980 | Horiba et al. | 250/343 |
| 4,253,770 | 3/1981 | Horiba | 250/343 |
| 4,598,201 | 7/1986 | Fertig et al. | 250/343 |
| 4,661,320 | 4/1987 | Ito et al. | 356/432 |
| 4,740,086 | 4/1988 | Oehler et al. | 250/343 |

FOREIGN PATENT DOCUMENTS 3509532 9/1986 Fed. Rep. of Germany .

Primary Examiner—Deborah L. Kyle
Assistant Examiner—J. Woodrow Eldred
Attorney, Agent, or Firm—Reed Smith Shaw & McClay

[57] ABSTRACT

This present invention pertains to a photo-acoustic apparatus for detecting energy that exits from the end of an optical fiber waveguide device. The photo-acoustic apparatus includes a housing having an opening through which the end of the optical waveguide device extends into the housing. The gas fills the housing and is capable of absorbing energy that exits the end of the optical waveguide device. The gas increases in pressure corresponding to the energy absorbed by it. There is also a pressure sensor such as a capacitor microphone disposed in said housing which is capable of sensing the pressure of the gas and producing an electric signal proportional to the energy which exits the optical waveguide device. Alternatively, a solid absorber is disposed in the housing that absorbs energy that exits from the end of the optical waveguide device. The gas filling the housing, in this case, does not absorb any of the energy.

8 Claims, 1 Drawing Sheet

PHOTO-ACOUSTIC DETECTOR

FIELD OF THE INVENTION

The present invention is related to a photo-acoustic detector. More specifically, the present invention is related to a photo-acoustic detector that has a capacitor microphone which senses the pressure of a gas. The pressure of the gas corresponds to the energy which exits an optical waveguide device.

BACKGROUND OF THE INVENTION

The use of optical waveguides, and specifically optical fibers, has become common in sensors of all types. One important aspect of these sensors is accurately detecting the energy that exits from the optical waveguide. Several methods have been devised to detect this energy. See Paul A. Willis; Industrial Research and Development, September, 1982.

These methods of detection all have difficulties in efficient energy conversion. Light energy to electrical energy conversion is inefficient because the modes of the radiation energy exiting from the end of the optical waveguide at large angles do not permit efficient energy coupling to these photodetectors.

SUMMARY OF THE INVENTION

The present invention pertains to a photo-acoustic apparatus for detecting energy that exits from the end of an optical fiber waveguide device. The photo-acoustic apparatus is comprised of a housing having an opening through which the end of the optical waveguide device extends into the housing. A gas fills the housing and is capable of absorbing energy that exits the end of the optical waveguide device. The gas increases in pressure corresponding to the energy absorbed by it. There is also a pressure sensor disposed in the housing which is capable of sensing the pressure of the gas and producing an electrical signal proportional to the energy which exits the optical waveguide device. Alternatively, a solid absorber is disposed in the housing that absorbs energy that exits from the end of the optical waveguide device. The gas filling the housing, in this case, does not absorb any of the energy.

BRIEF DESCRIPTION OF THE PREFERRED EMBODIMENT

Figure 1:
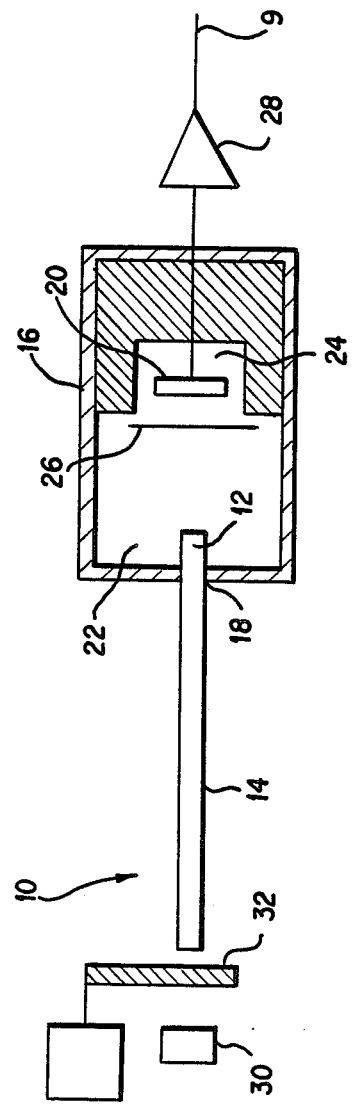
FIG. 1 is a schematic representation of the photo-acoustic apparatus.

There is shown a photo-acoustic apparatus 10. The photo-acoustic apparatus 10 detects energy that exits from the end 12 of an optical waveguide device 14 such as an optical fiber or an optical fiber bundle. The photo-acoustic apparatus 10 comprises a housing 16 having an opening 18. The end 12 of the optical waveguide device 14 extends through the opening 18 into the housing 16. Preferably the housing 16 is hermetically sealed and the opening 18 in the housing 16 is capable of sealably receiving the end 12 of the optical waveguide device 14.

A gas fills the housing 16 and is capable of absorbing energy that exits the end 12 of the optical waveguide device 14. The gas increases in pressure corresponding to the energy absorbed.

The photo-acoustic detector 10 is also comprised of a pressure sensor such as a capacitor microphone 20 which is disposed in the housing 16. The capacitor microphone is capable of sensing the pressure of the gas and producing an electrical signal proportional to the energy which exits the optical waveguide device 14.

Preferably the housing 16 has a first chamber 22 and a second chamber 24. The second chamber 24 communicates with the first chamber 22. The capacitor microphone 20 is preferably disposed in the second chamber 24 and the opening 18 in the housing 16 preferably communicates with the first chamber 22.

The photo-acoustic apparatus 10 preferably also is comprised of a highly reflective shield 26 disposed in the housing 16 between the end 12 of the optical waveguide device 14 and the capacitor microphone 20. The highly reflective shield 26 reduces black body absorption. There is also an amplifier 28 electrically connected to the capacitor microphone 20 for amplifying the signal produced by the capacitor microphone 20.

The photo-acoustic apparatus 10 can also include a light source 30 disposed such that light produced therefrom enters the optical waveguide device 14. An interruptor 32 disposed between the light source 30 and the optical waveguide device 14, can be used to interrupt or chop the light entering the optical waveguide device 14.

The photo-acoustic apparatus 10 can be used to selectively detect energy at a specific wavelength. In one embodiment, the gas filling the housing 16 absorbs energy that exits from the end 12 of the optical waveguide device 14 only at a specific wavelength. In another embodiment of the photo-acoustic apparatus 10 with respect to selective detection, a gas fills the housing 16 which does not absorb energy exited from the end of the optical waveguide device 14. A solid absorber 34 preferably having a hemispherical shape, is disposed in the housing 16 such that it receives the energy which exits the end 12 of the optical waveguide device 14. The solid absorber 34 which absorbs energy at a select wavelength, is heated by the energy. The solid absorber 34 in turn heats the gas causing the pressure of the gas to increase. For example, if the energy to be detected is in the visible or infrared region, argon can be used as the gas which fills the housing 16. The embodiment of the photo-acoustic apparatus 10 having a solid absorber 34 can be used to non-selectively detect the energy exiting from the end 22 of the optical waveguide device 14 if the solid absorber 34 has black body absorption characteristics. Such a solid absorber 34 could be carbon black.

The photo-acoustic apparatus 10 can also have a second optical waveguide device and a second housing, similar to the optical waveguide device and housing described above. The second optical waveguide device extends through the opening in the second housing. The optical waveguide devices 14 are then reference and sensor optical waveguide devices of the photo-acoustic apparatus 10 and can be used as described in U.S. Pat. Nos. 3,180,984 to Fertig et al. and 4,608,344 to Carter et al. The light source 30 and interruptor 32 is common to the sensor and reference optical waveguide devices.

In a preferred embodiment, the photo-acoustic apparatus 10 is used to determine the level of carbon dioxide dissolved in a liquid. The liquid is placed on the surface of the optical waveguide device 14. A portion of the light passing through the optical waveguide device 14 escapes into the liquid, then due to the index of refraction of the liquid, the light that has escaped the optical waveguide device 14 is bent and re-enters the optical waveguide device 14. If there is dissolved carbon dioxide in the liquid, a portion of the light propagating through the optical waveguide device 14 is absorbed in the liquid. The photo-acoustic apparatus 10 is made selective to the detector of carbon dioxide by filling the housing 16 with carbon dioxide gas. Then the energy exiting the end 12 of the optical waveguide device 14 is absorbed by the gas causing a proportional increase in the pressure of the gas. The signal produced by the capacitor microphone 20 is calibrated based on the dissolved carbon dioxide in the liquid.

While the preferred embodiment provides an example of detecting dissolved carbon dioxide in a liquid, the photodetector apparatus 10 can be used to analyze any liquid or solid that selectively absorbs light energy.

What is claimed is:

1. A photo-acoustic apparatus for detecting energy that exits from the end of an optical waveguide device comprising:
   a non-porous housing having an opening through which the end of the optical waveguide device extends into the housing;
   a known gas which fills the housing and which is capable of absorbing energy that exits the end of the optical waveguide device, said gas increasing in pressure corresponding to the energy absorbed; and
   a pressure sensor disposed in said housing which is capable of sensing the pressure of the gas and producing an electrical signal proportional to the energy which exits the optical waveguide device.

2. A detector as described in claim 1 wherein the housing is hermetically sealed and the opening in the housing is capable of sealably receiving the ends of the optical waveguide device.

3. A detector as described in claim 2 wherein the housing has a first chamber and a second chamber in communication with the first chamber, said pressure sensor disposed in the second chamber, said opening in the housing communicating with the first chamber, and including a highly reflective shield disposed in said housing between the end of the optical waveguide device and the pressure sensor.

4. A detector as described in claim 3 wherein the pressure sensor is a capacitor microphone.

5. A detector as described in claim 4 wherein the pressure sensor is a capacitor microphone including an amplifier electrically connected to the capacitor microphone for amplifying the signal produced by the capacitor microphone.

6. A detector as described in claim 5 wherein the gas absorbs energy at a predetermined wavelength.

7. A detector as described in claim 6 including an interruptor to interrupt the energy entering the optical waveguide device.

8. A detector as described in claim 7 including a light source disposed such that light produced therefrom enters the optical waveguide device after passing through the interruptor.

* * * * *